United States Patent [19]

Kurtz et al.

[11] Patent Number: 4,735,901

[45] Date of Patent: Apr. 5, 1988

[54] **TRANSFORMATION OF *CANDIDA ALBICANS***

[75] Inventors: Myra B. Kurtz, Martinsville; Donald R. Kirsch, Princeton, both of N.J.

[73] Assignee: E. R. Squibb & Sons, Inc., Princeton, N.J.

[21] Appl. No.: 691,303

[22] Filed: Jan. 14, 1985

[51] Int. Cl.$^4$ .................... C12N 15/00; C12N 5/00; C12N 7/00

[52] U.S. Cl. .................... 435/172.3; 435/255; 435/922; 435/320; 935/28; 935/37; 935/69; 536/27

[58] Field of Search .................... 435/172.3, 317, 255, 435/922; 935/69, 37, 28

[56] References Cited

U.S. PATENT DOCUMENTS

| | | | |
|---|---|---|---|
| 4,374,927 | 2/1983 | Sninsky et al. | 435/68 |
| 4,613,572 | 9/1986 | MacKay et al. | 435/255 |
| 4,628,033 | 12/1986 | De Zeeuw et al. | 435/317 |

OTHER PUBLICATIONS

N. J. W. Kreger-van Rij *the Yeasts: A Taxonomic Study,* Elsevier Science Publ. Amsterdam, 1984, pp. 2, 3, 10, 37 and 38.

Hinnen, A., J. B. Hicks, G. R. Fink, *Proc. Natl. Acad. Sci.* U.S.A. 75(4), 1929–1933, 1978.

Sherman, F., G. R. Fink, J. B. Hicks, *Methods in Yeast Genetics* Cold Spring Harbor Laboratory, N.Y. 1982, pp. 106–114.

Struhl, K., D. T. Stinchcomb, S. Scherer and R. W. Davis *Proc. Natl. Acad. Sci.* U.S.A. 76(3), 1035–1039, 1979.

Poulter, R. T. M. and E. H. A. Rikkerink. *Journal of Bacteriology* 156(3): 1066–1077, 1983.

Savsnauskas, K. et al., *Academy of Sciences of the Lithuanian SSR Dokl Biochem* 263:60–62, 1982.

Orr-Weaver, T. L. J., W. Szostak and R. J. Rothstein *Proc. Natl. Acad. Sci.* U.S.A. 78(10): 6354–6358, 1981.

Gillum, A. M., E. V. H. Tsay and D. R. Kirsch *Mol. Gen. Genetics* 198: 179–182, 1984.

*Primary Examiner*—Thomas G. Wiseman
*Assistant Examiner*—Robin Teskin
*Attorney, Agent, or Firm*—Lawrence S. Levinson; Donald J. Barrack

[57] ABSTRACT

*Candida albicans* has been transformed by the insertion of a plasmid comprising a fragment of DNA from *Candida albicans* containing the intact ADE 2 gene.

7 Claims, 4 Drawing Sheets

TRANSFORMATION OF *CANDIDA ALBICANS*

BACKGROUND OF THE INVENTION

*Candida albicans* is a human pathogen which causes mild diseases such as vaginitis and thrush in patients with normal immune systems, but which is life-threatening in immuno-deficient patients. With the increasing use of chemotherapy in cancer treatment, immuno-compromised patients have become more common. The usual therapy for systemic candidal infections is amphotericin B, a polyene antibiotic. However, this drug concentrates in the liver and can cause damage, especially in patients on chemotherapy and in the elderly. The need for improved therapy has spurred research for new anticandidal drugs. A preferred source for completely novel structures with antibiotic activity is fermentation broths of microorganisms found in the wild, as well as other natural products. The classical method for screening these products is the disc diffusion test in which the broth is placed in a well or on a paper disc and allowed to diffuse into the solid growth medium seeded with the test organism. After growth, potential antibiotics are revealed by a zone of killing surrounding the disc. The size of the zone is determined both by the concentration and efficacy of the antibiotic. The classical test has several limitations for detecting new drugs. Since this test has been used for years by many pharmaceutical companies, most, if not all, of the easily detected antibiotics such as polyenes have been isolated. If a good drug is produced in very low quantities, it can be missed in the conventional assay. Even with increased sensitivity, the diffusion assay cannot discriminate between agents that are toxic for humans and those that are specific for fungi. Thus, a primary goal of screen development is sensitive and specific assays. One powerful tool for devising sensitive screens is manipulating the test organism genetically. For example, Selitrennikoff has published a screen for fungal cell wall inhibiting agents based upon the unique behavior of a mutant (os-1) of the fungus *Neurospora crassa* [Selitrennikoff, Anti. Micro. Agents and Chemo., 23, 727, (1983)]. This kind of screen is of great interest because it is unlikely that agents specific for fungal cell walls would be harmful to humans. Other specific screens using mutant test organisms are in use. There are significant differences in cell wall structure and physiology between *Candida albicans* and fungi with well-characterized genetic systems such as *Neurospora crassa*. This makes development of means for genetic manipulation of Candida highly desirable. Genetic manipulations of *Candida albicans* have been hampered by several factors:

1. It is difficult to obtain recessive mutations due to the diploid nature of the organism.
2. There is no sexual cycle for recombination.
3. The parasexual cycle is laborious, requiring protoplast fusion of suitably marked auxotrophic strains.
4. No method for introduction of DNA either as plasmid vectors or linear DNA fragments has been found.

After the discovery that DNA could be reliably introduced into the bakers yeast *Saccharomyces cerevisiae* by plasmid vectors and linear DNA, transformation systems for other fungi seemed feasible. With the appropriate vector/host pair, genes from diverse sources such as bacteria, fungi and mammalian cells have been cloned and expressed in Saccharomyces. Mutations have been introduced with plasmids by gene disruption and by in vitro mutagenesis. Very high levels of normal yeast enzymes have been obtained by cloning yeast genes on high copy number plasmids and hybrid gene products have been produced by fusion of yeast DNA sequences with foreign DNA such as the bacterial gene for $\beta$-galactosidase. Therefore, transformation provides a method for introducing a wide variety of genetic alterations into an organism.

Development of a transformation system for *Candida albicans* has been difficult because a suitable vector/host system has not been available. The vector must have a selectable marker because transformation generally occurs at a low frequency and detection would otherwise be unacceptably laborious. Two types of selectable markers are known: genes conferring resistance to an antibiotic to a sensitive host, and wild-type genes complementing auxotrophic mutations in the recipient host. Due to the natural resistance of Candida to most antibiotics, the complementation approach is more feasible. The Candida gene for orotidine-5'-phosphate decarboxylase has recently been isolated by complementation of an auxotrophic mutant in a heterologous host (A. Gillum, E. Tsay, and D. R. Kirsch, *Mol. Gen. Genetics*, 198(1) pgs 179–182 (1984)). However, it was not possible to isolate the proper Candida host strain with the equivalent mutation.

SUMMARY OF THE INVENTION

A process has been devised for producing genetically engineered *Candida albicans* strains which can be used as a research tool for studying the clinically important yeast *Candida albicans*. This process for introducing exogenous DNA into *Candida albicans* comprises:

(i) enzymatically removing the cell wall of *Candida albicans*;

(ii) adding exogenous DNA to the resultant *Candida albicans*;

(iii) fusing the exogenous DNA with the *Candida albicans*; and (iv) incubating the *Candida albicans* having the exogenous DNA incorporated therein to allow expression of the DNA and to regenerate the cell wall.

A set of fragments of DNA from *Candida albicans* containing the intact gene specifying aminoimidizole ribotide decarboxylase (ADE 2), an essential enzyme in the biosynthetic pathway for adenine, have been cloned. Plasmid cloning vehicles containing these fragments, therefore, have a selectable marker for transformation of *Candida albicans* hosts with the appropriate ade 2 mutation. Transformants are selected by their ability to grow without adenine supplementation. Examples of plasmids containing the Candida ADE 2 DNA are described herein.

The plasmids provide vectors for producing mutations in *Candida albicans* for use in the screening of chemical compounds for antifungal activity. Strains carrying these mutations are more susceptible to antifungal agents, and therefore, allow compounds present in minute quantities in nature to be recognized as antifungal agents. They also facilitate the discovery of compounds which are targeted to *Candida albicans* and which do not attack the host.

DETAILED DESCRIPTION OF THE INVENTION

Figure 1:
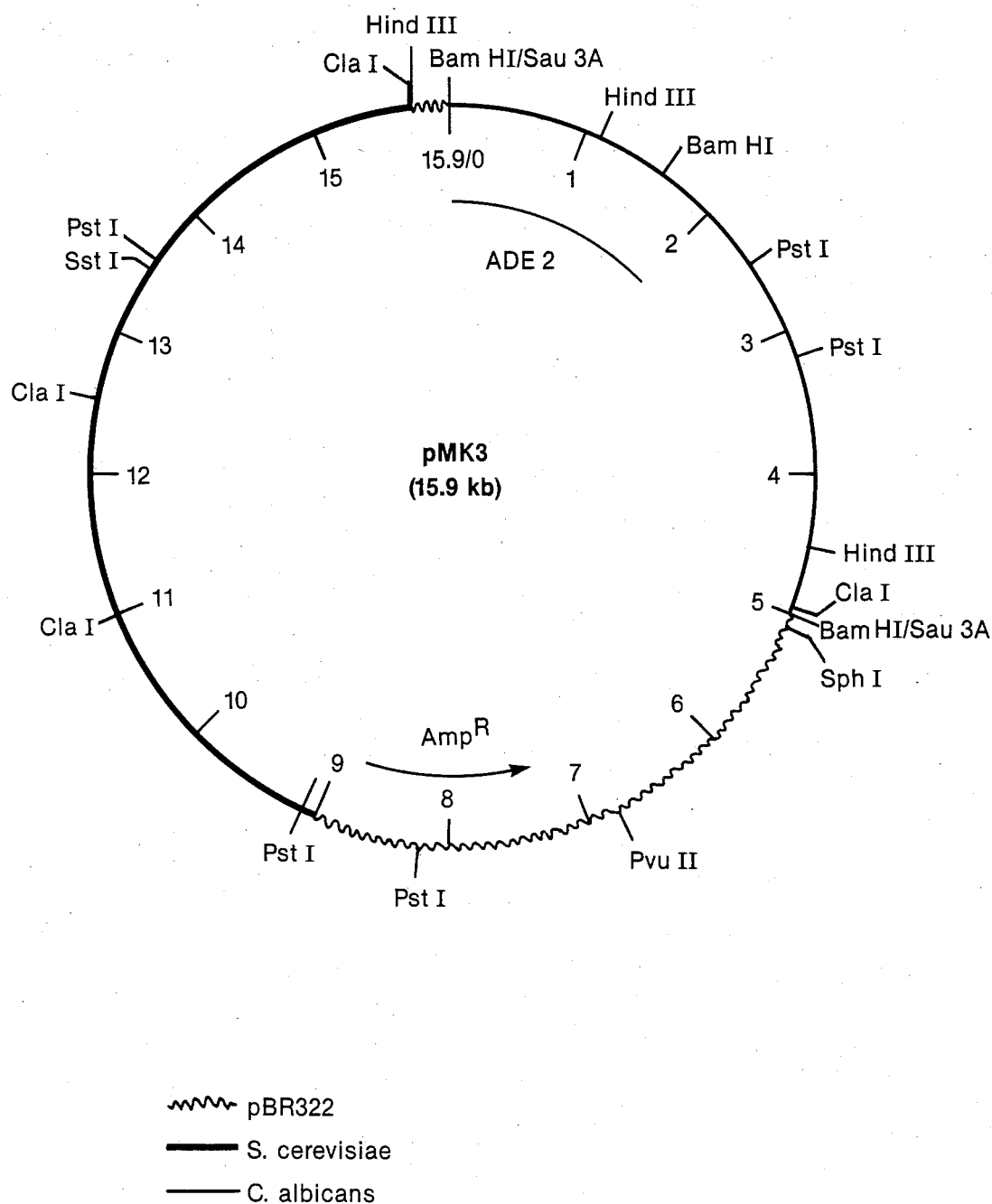
FIG. 1 illustrates the structure of recombinant plasmid pMK3.

The process of this invention provides for the introduction of exogenous DNA into *Candida albicans*. Initially, the cell wall of the recipient *Candida albicans* is enzymatically removed. This can be accomplished by first growing and harvesting the *Candida albicans* cells, incubating these cells with a sulfhydryl reagent (e.g., β-mercaptoethanol or dithiothreitol), and then treating the cells with cell wall lytic enzyme (e.g., snail gut enzyme or zymolase).

The *Candida albicans* cells (with cell walls removed) are combined with exogenous DNA which is then fused with the cells using a fusing agent such as polyethylene glycol 4000. The addition and fusing of exogenous DNA to the *Candida albicans* cells is accomplished by first heating the cells briefly (less than about 1 minute) at 37° C. with dimethylsulfoxide and then placing them in an ice bath. The exogenous DNA is then added, the mixture is incubated on ice for about 30 minutes to 1 hour, and heated briefly (less than about 1 minute) at 42° C. The addition of DNA can also proceed without the 37° C. heat treatment, the incubation on ice and the 42° C. heat shock. The fusing agent is then added, the mixture incubated at room temperature and the fusing agent removed by washing. The *Candida albicans* cells with fused exogenous DNA are incubated in fully supplemented growth medium for at least about 30 minutes to 1 hour to allow the expression of the exogenous DNA and the start of regeneration of the cell walls. After initiating cell wall regeneration, the *Candida albicans* cells are plated on osmotically supported selective medium to select transformants which have incorporated the exogeneous DNA.

The strategy for cloning the Candida ade 2 gene is as follows. Total genomic DNA from a wild-type Candida strain can be isolated by published procedures [D. R. Cryer, R. Eccleshell and J. Marmur, Methods Cell Biol. 12:39 (1975)] to give high molecular weight DNA. This DNA contains the ADE 2 gene as well as all the other Candida genes. As isolated, the DNA fragments are too large for cloning into vectors and must be made smaller without damaging the gene of interest. More than one method is available for generating random breaks in the DNA. The preferred method involves cutting the DNA with a restriction enzyme (Sau 3A), which cuts very frequently along the entire length of the DNA. To ensure that at least some copies of the ADE 2 gene are not cut, the condition used allows only partial digestion which randomizes the cutting. DNA fragments large enough to contain several adjacent intact genes (5–20 kb) are isolated on a sucrose gradient (T. Maniatis, E. E. Fritsch and J. Sambrook "Molecular Cloning", Cold Spring Harbor, 1982). Since the enzyme used generates cohesive ends compatible with those generated by restriction enzyme Bam HI, the Candida DNA fragments could be cloned into any vector with a Bam HI site such as the well-known cloning vector YEp13. Several other enzymes produce compatible cloning sites in a variety of vectors such as Bcl I, Bgl II, Mbo I and Xho II. Other enzymes which cut frequently (i.e., recognize a specific 4 bp sequence instead of a 6 bp sequence) such as Rsa I and Taq I can also be used to generate random fragments of Candida DNA. Alternatively, random shear can be used to generate random fragments.

A library constructed of Candida fragments in vector YEp13 can be screened for ADE 2 DNA by complementation of a Saccharomyces strain with a mutation in the gene equivalent to that of the Candida ADE 2. *Saccharomyces cerevisiae* strain W343-4A (MAT alpha ade 2-1, can 1-100, ura 3-1, leu 2-13, 2-112, lys 2-1, his 3-11, 3-15) carrying the mutation ade 2-1 and *Saccharomyces cerevisiae* strain XMK1-222 (MATa ade 2-5, leu 2-2, 2-112, his 3-11, 3-15, arg 4, thr 1, cup $1^s$) carrying ade 2-5 are examples of suitable mutant Saccharomyces strains. This procedure can also be performed on other strains carrying ade 2 mutations. Strains carrying ade 2 mutations are widely available and can be obtained from the Yeast Genetic Stock Center, University of California, Berkeley Calif. 94720. After the Saccharomyces strain is transformed with a YEp13 Candida library by standard techniques [J. D. Beggs, Nature 275:104 (1978)], all plasmid-containing transformants are selected by virtue of the Saccharomyces LEU2 gene on the YEp13 vector complementing the leu 2 double mutations in the recipient strains. Strains able to grow without leucine supplementation are screened for adenine prototrophy on minimal medium. Libraries constructed in other yeast cloning vectors can also be used, requiring the appropriately marked recipient strain to select for the initial transformants. Plasmids pMK3 and pMC1 were obtained by this method and are examples of ADE 2 containing plasmids obtained in YEp13. The ADE 2 complementing activity can be subcloned into a variety of vectors by choosing the appropriate restriction enzyme. The 5.2 kb insert fragment common to both pMK3 and pMC1 indicate the maximum limits of the ADE 2 gene. The minimum limits can be determined by further subcloning. pMC2 is an example of subcloning the maximum limit ClaI fragment from pMK3 into a well-known vector pBR322 [Bolivar et al., Gene:2:95 (1977)]. pSM7 is an example of subcloning a smaller portion of the ADE 2 region, the 2.5 kb EcoRV fragment from pMC2 into pBR322 which also has complementing activity.

The 5.2 kb cloned fragment common to pMC1 and pMK3 is derived from Candida chromosomal DNA as demonstrated by hydridization analysis with gel fractionated restriction digests of *Candida albicans, Escherichia coli, Saccharomyces cerevisiae* and bacteriophage lambda DNA probed with $^{32}P$ labelled pMC1 and YEp13. There are no sequences homologous to Candida DNA in YEp13, but pMC1 hybridizes to Candida DNA in the pattern predicted from the restriction map of the insert. For example, Hind III cut *Candida albicans* DNA probed with pMC1 yields a 3.4 kb fragment which is the same as the 3.4 kb internal piece of pMC1 and has two larger fragements corresponding to the two flanking sequences. The expected number and size of bands are also found with Pvu II and EcoRV cut Candida DNA as well as with other enzymes.

The Candida ADE 2 gene can be used as a selectable transformation marker for *Candida albicans*. The Candida transformation method of this invention requires logarithmically growing cells of an ade 2 strain of Candida at a density of $0.5-4 \times 10^7$/ml. The cells are harvested by centrifugation and incubated with a sulfhydryl reagent in an osmotically supportive medium (1M sorbitol, 50 mM dithiothreitol, 25 mM EDTA pH 8.0)

for 10–20 minutes at 30° C. The cells are washed and resuspended in buffer suitable for the cell wall lytic enzyme used (0.1 M sodium citrate pH 5.8, 1 M sorbitol, 25 mM EDTA for snail gut enzyme, or 0.01 M Tris HCl pH 7.5, 1 M sorbitol, 25 mM EDTA for zymolyase). The spheroplasts formed after 30–60 minutes are washed and resuspended in CaS (1 M sorbitol, 10 mM $CaCl_2$, 10 mM Tris HCl pH 7.5). Either of two procedures may be followed at this point. In procedure A, 1/100 volume of dimethylsulfoxide is added to the spheroplast suspension. The spheroplasts are heated for 30 seconds at 37° C. and then placed in an ice bath. Vector DNA is added to the treated spheroplasts, incubated on ice for 30–45 minutes, heated at 42° C. for 30 seconds and 10 volumes of polyethylene glycol 4000 (20% solution W/V) are added. The mixture is incubated at room temperature for 20 minutes and washed free of polyethylene glycol. The spheroplasts are resuspended in fully supplemented minimal medium for at least about 30–60 minutes (to allow the expression of the ADE 2 gene and the start of regeneration of the cell walls) and plated on suitable selective medium (0.67% Bacto-Yeast nitrogen base without amino acids, 2% dextrose, 2% agar) with appropriate osmotic support. In procedure B, the vector DNA is added to the spheroplast suspension in CaS, incubated for 15 minutes at room temperature, after which 10 volumes of polyethylene glycol 4000 (20% solution W/V) is added. The mixture is incubated at room temperature for 15 minutes and then washed free of polyethylene glycol. The remainder of the procedure is the same as above. The transformation frequencies of *Candida albicans* strain hOG300 (ade 2, met, pro, bio) ranged between 0.5–10 transformants/μg DNA (Table I).

TABLE I

Transformation Frequencies of hOG300

| Plasmid DNA | Quantity of DNA | #ade+ | #ade+ with YEp13 Sequences | per/μg DNA |
|---|---|---|---|---|
| pMC1 | 5 μg | 1 | 1 | 0.2 |
| pMK3 | 5 μg | 2 | 0 | 0 |
| pMK3 | 56 μg | 30 | 12/26 | 0.53 |
| pMC2 | 2.5 μg | 13 | 4–7$^1$/13 | 5.2 |
| 0 | — | 0–2$^2$ | 0 | — |

The presence of YEp13 sequence was determined by colony dot blots for the number of isolates indicated.
1. Four of the colonies gave strong hybridization, while 3 had weaker signals.
2. The appearance of ade+revertants was 0, 1 and 2 in three separate experiments.

Since strain hOG300 grows poorly on supplemented minimal medium, a faster growing spontaneous derivative was selected. This strain, DKY-129, has lost the methionine marker of the parent strain but retains the proline, biotin and adenine requirements. It transforms at the same frequency as hOG300, but grows better and produces more red pigment enabling rapid identification of ADE+(white) transformants. The presence of YEp13 sequences in the adenine prototrophs was scored by hydridization with a radiolabelled probe by colony hybridization analysis.

A subculture of The *Candida albicans* strain DKY-129 may be obtained from the permanent collection of the American Type Culture Collection, Rockville, Maryland. Its accession number in this repository is A.T.C.C. No. 20,735.

Colony hybridization of *Candida albicans* was performed by slight modification of the procedure described for *Saccharomyces cerevisiae* [A. Hinnen, B. Hicks and G. R. Fink, Proc. Natl. Acad. Sci. 75:1929 (1978)]. Colonies to be tested were streaked on YEPD (1% yeast extract, 2% peptone, 2% glucose), solidified with 2% agarose, grown for 2 days at 30° C, and transferred to Gene Screen membranes (New England Nuclear, Boston, Mass.) by overlaying with the membranes for one day. The transferred cells were lysed in-situ with zymolase (Miles, Naperville, Ill.) and the DNA containing membranes were treated according to the procedures recommended by the manufacturer. Hybridizations with DNA labelled by nick translation were performed by standard procedures (T. Maniatis, op cit). Approximately 50% of the prototrophs obtained by transformation with pMK3 gave a positive signal with the YEp13 probe, while all were positive with a pMK3 probe.

Similar results are obtained from transformations with pMC2. The strains lacking YEp13 sequences could either be due to reversion of the ade 2 lesion, to a double crossover event at the chromosomal gene, gene conversion or a single crossover followed by a precise excision of the ade 2 allele and the YEp13 sequences. However, the appearance of ADE 2+ colonies in these experiments is ten-fold greater than the reversion rate, making reversion unlikely.

Total DNA prepared from pMK3 transformants with YEp13 sequences were further analyzed by gel blots. Undigested, Cla I, Pvu II, Hind III, Sph I, BamHI and EcoRV - digested DNAs were hybridized with radiolabelled YEp13, pMK3 or pMC1 DNA. The results of these experiments showed that hybridization of YEp13 with undigested DNA occurred at the position of chromosomal DNA indicating that these sequences had been integrated into the genomic DNA. No hybridization with lower molecular weight bands could be observed even with extended exposure of the autoradiograms. Restriction analysis indicated that the transformants arose by a single recombination event at the homologous region, retaining the entire YEp13 sequence. For example, Cla I digestion of pMK3 yields four fragments of 5.2, 6.0, 2.5 and 2.0 kb. These four bands plus the two flanking fragments at the site of integration should be revealed when Cla 1 cut DNA from the transformants is hybridized with labelled pMK3. When probed with pMK3, transformant DNA showed the expected two additional bands which have the same mobility as the host ADE 2 region band. No other bands are seen. These results are consistent with one or several tandem copies integrated at the site of the resident ade 2 gene.

Similar conclusions can be drawn from the BamHI, EcoRV and HindIII digestion results. Twenty-six pMK3 transformants were tested for stability by growing for 20 generations in rich medium and plating onto selective and non-selective media. No ade 2− segregates were detected for 24 of the strains (>100 isolates tested). Two of the strains gave rise to ade 2− segregants at a rate of 1% and 5%. These results are also consistent with an integrative transformation event.

The general utility of the invention is demonstrated by transformation of other *Candida albicans* red adenine auxotrophs. The biochemical nature of the lesions in mutants isolated by Kwon-Chung & Hill [Sabouradia 8:48–59 (1970)] have not been determined. One of these, *Candida albicans* strain A81-Pu, is transformed by pMC2 at a frequency of 1.5 transformants/μg DNA. This strain is derived from an entirely separate lineage from DKY-129. The parent of A81-Pu was a clinical isolate maintained for several years at the Medical Mycology Section, National Institute of Health, Bethesda, Md. The transformation method is, therefore, not limited to a single *Candida albicans* strain.

The number of putative transformants by this invention increases with increasing amounts of plasmid DNA added. Transformation frequencies were consistently higher with pMC2 and pSM7 than with pMK3 or pMC1. In addition, transformation frequencies can be enhanced in several ways:

1. Linearizing the plasmid by restriction endonuclease cutting just outside the complementing region, but within the region of homology increases the frequency 3–5 fold.
2. Addition of sonicated non-transforming DNA such as commercially available *Escherichia coli* DNA enhances the frequency per μg plasmid DNA by 6–10 fold.
3. Cloning of certain *Candida albicans* sequences in ADE 2 containing vectors increases transformation frequencies up to ten fold.

These factors can be additive resulting in transformation frequencies of greater than 200 transformants per μg plasmid DNA.

A further utility of the method of this invention is cloning DNA adjacent to regions already cloned. If one gene of a cluster of genes has been cloned, the adjacent genes can be obtained from a transformant with an intact plasmid integrated near the gene of interest. For example, the map of pMK3 integrated into *Candida albicans* strain (ade 2, pro, met, bio) hOG300 indicates that cutting chromosomal DNA with BamHI and ligating the DNA under dilute DNA concentration, conditions which promote self-ligation, pMK3 will be reformed. Similarly, cutting PvuII or SphI will generate new plasmids containing regions of the Candida chromosome not previously cloned.

The following examples are specific embodiments of this invention.

EXAMPLE 1

Recombinant Plasmid pMK3

A library of Candida DNA fragments produced by partial digestion with restriction enzyme Sau 3A cloned into the Bam HI site of YEp13 (A. Gillum, E. Tsay, and D. R. Kirsch, *Mol. Gen. Genetics*, 198(1) pgs 179–182 (1984)) was used to derive pMK3. A strain of *Saccharomyces cerevisiae*, XMK1-222 (MATa ade 2-5, leu 2-2, 2-112, his 3-11, 3-15, arg 4, thr 1, cup $1^s$) with a mutation at the ade 2 locus (ade 2-5) and a double mutation at the leu 2 locus was transformed with 30 μg of library DNA according to Beggs [Nature (1978) 275:104–109]. Leucine prototrophs were selected in minimal medium (F. Sherman, G. R. Fink, and J. B. Hicks, "Methods in Yeast Genetics", Cold Spring Harbor, 1983). Approximately $10^6$ leucine prototrophs in 2.5% top agar were harvested into 75 ml sterile water, homogenized briefly and plated onto medium without adenine or leucine. Colonies capable of growth without adenine were purified, the plasmids were recovered (F. Sherman et al., op cit) and used to transform *E. coli* RR1 cells, A.T.C.C. No. 31447, by standard procedures (T. Maniatis et al., op cit). The plasmids were amplified in *E. coli* RR1 cells, purified, and used to transform ade 2 *S. cerevisiae* strains W343-4A and XMK1-222 to adenine prototrophy. Strain W343-4A has the following genotype: MAT alpha ade 2-1, can 1-100, ura 3-1, leu 2-3, 2-112, lys 2-1, his 3-11, 3-15. Strain XMK1-222 has the following genotype: MATa ade 2-5, leu 2-2, 2-112, his 3-11, 3-15, arg 4, thr 1, cup $1^s$. pMK3 was identified as a plasmid carrying an insert capable of complementing ade 2-1, and ade 2-5 mutants of *S. cerevisiae*. Confirmation that the insert is Candida DNA was obtained by hybridization of DNA transferred from agarose gels to nylon membranes by the procedure of Southern (T. Maniatis et al., op cit). Total DNA from *S. cerevisiae* was obtained by standard procedure [R. W. Davis et al., "Methods in Enzymology", 65:404 (1980)] and *E. coli* B DNA was purchased from Sigma (St. Louis, Mo.). Total Candida DNA was isolated from 50 ml of a late log culture according to the following procedure. Cells were pelleted and washed with 2.0 ml SCE (1M sorbitol, 0.1 M sodium citrate, pH 5.8, 25 mM EDTA) and resuspended in 0.75 ml SCE. Cell wall digestion was achieved by first adding 5 Aμl β-mercaptoethanol and allowing the cells to incubate at room temperature for 10 minutes. Then 50 μl of 3 mg/ml zymolyase 5000 (Miles, Naperville, Ill.) in SCE was added and the mix was incubated at 37° C. for 40 minutes. The cells were washed free of the enzyme and resuspended in 0.75 ml of 4.5 M guanidine HCl, 0.1 M EDTA, 0.15 M NaCl, pH 8.0. Ten percent sarcosyl was added to 0.5% final concentration and incubated at 65° C. for 10 minutes. One volume of cold absolute ethanol was added and the DNA spun down immediately for 30 seconds at 10,000 rpm. The pellet was resuspended in 10xTE (1xTE=10 mM Tris HCl pH 8.0, 1 mM EDTA) and extracted once with phenol:chloroform:isoamyl alcohol (25:24:1). The aqueous phase was precipitated overnight at 4° C. with 0.6 volume of isopropanol. The precipitate was recovered by centrifugation and extracted five times with phenol:chloroform:isoamylalcohol (25:24:1). The final aqueous phase was ethanol precipitated and resuspended in 50 μl TE. $^{32}P$ labelled pMK3 and $^{32}P$ labelled YEp13 were prepared by nick translation (T. Maniatis et al., op cit) and hybridized to DNA gel blots of *E. coli*, *S. cerevisiae* and *Candida albicans* DNA. The result of these experiments indicate that the insert is Candida DNA. Restriction endonuclease mapping resulted in the structure indicated in FIG. 1. Comparison of the Southern hybridization data of pMK3 cut with HindIII, BamHI, and ClaI to Candida chromosomal DNA cut with these enzymes indicates that the cloned fragment does not have any major rearrangements relative to the chromosomal sequence.

EXAMPLE 2

Recombinant plasmid pMC1

Figure 2:
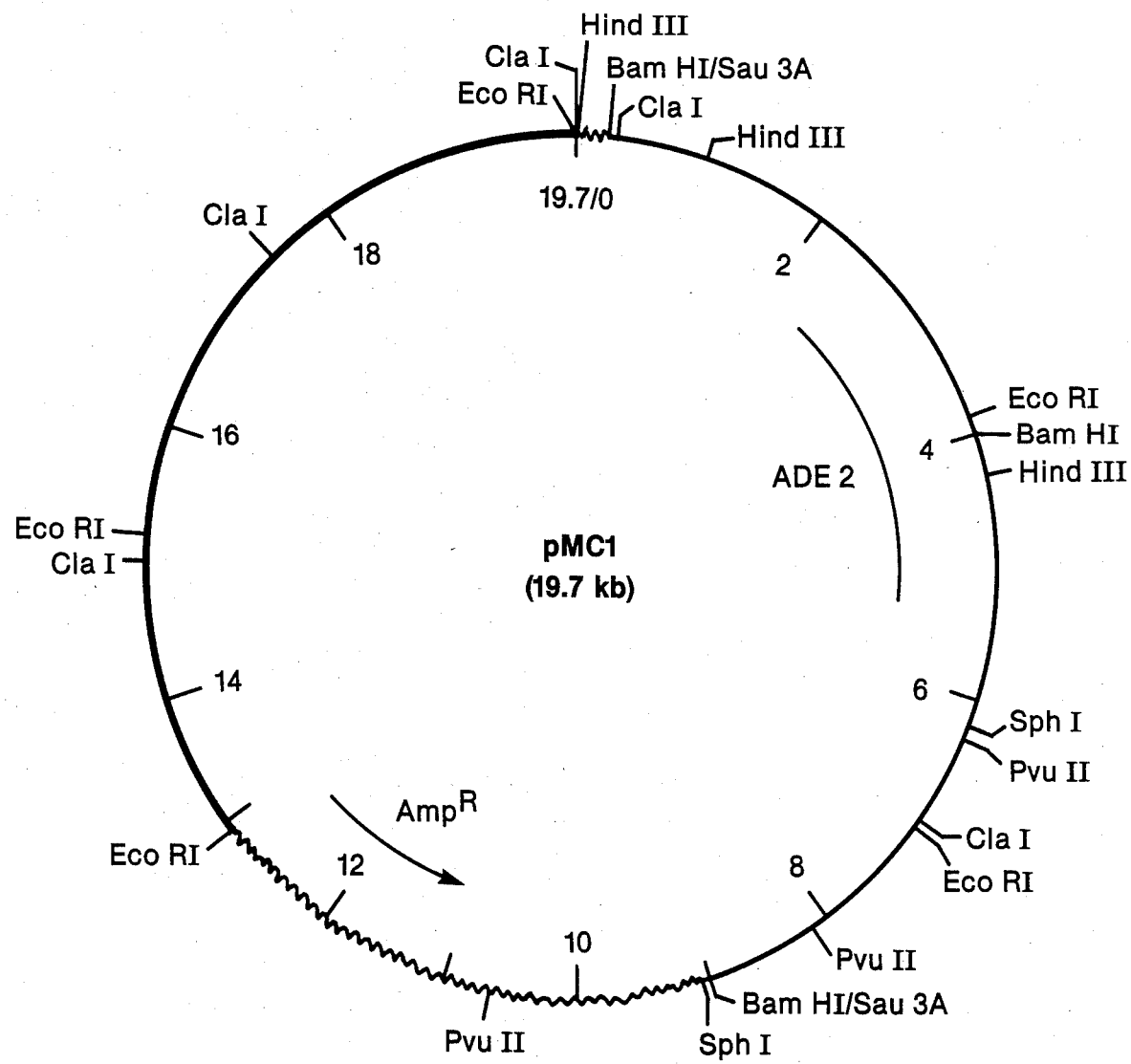
FIG. 2 illustrates the structure of recombinant plasmid pMC1.

The Candida Sau 3A partial library in YEp13 described in Example 1 was used to transform *Saccharomyces cerevisiae* strain W343-4A (MAT alpha, ade 2-1, can 1-100, ura 3-1, leu 2-3, 2-112, lys 2-1, his 3-11, 3-15) by the procedure described in Example 1. Since the library consisted of random fragments of Candida DNA in YEp13 and since each transformation selected a subpopulation of the entire collection, a different plasmid was obtained in this Example. Plasmid pMC1 was recovered by this procedure and the Candida insert has the restriction map indicated in FIG. 2.

EXAMPLE 3

Recombinant plasmid pMC2

Figure 3:
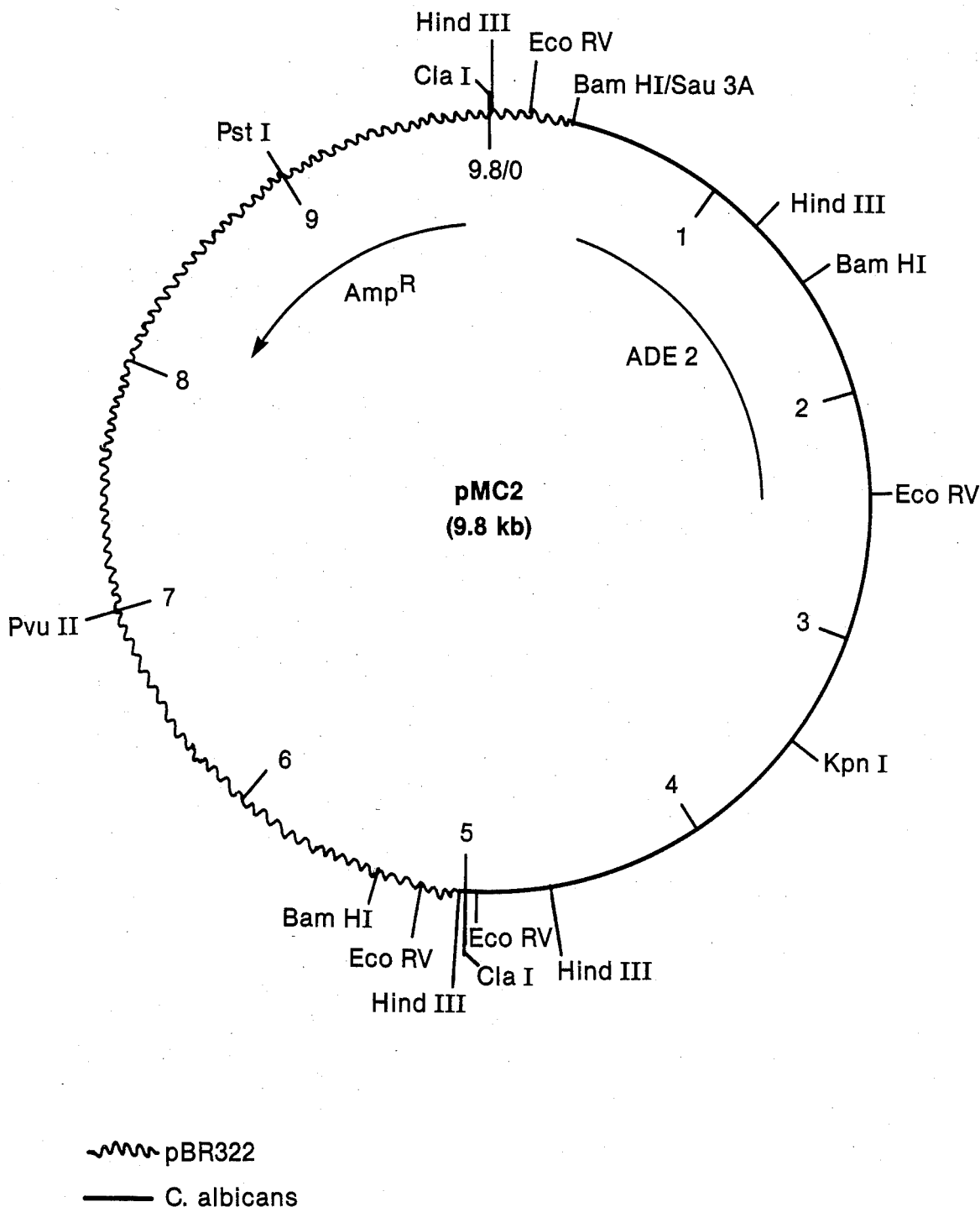
FIG. 3 illustrates the structure of recombinant plasmid pMC2.

The construction of pMC2 was accomplished by combining the 5.2 kb Cla I fragment of pMK3 derived from Candida DNA with a small portion of YEp13 DNA and the cloning vehicle pBR322 [F. Bolivar et al., Gene 2:95 (1977)]. 0.5 μg of pBR322 was cut with restriction enzyme Cla I using low salt buffer conditions (T. Maniatis et al., op cit) and then treated with calf intestinal alkaline phosphatase to prevent self-ligation (according to manufacturers recommendation, Boehringer Mannheim, Indianapolis, Id.). 8 μg of pMK3 was digested with Cla I and the appropriate Cla I fragment cut out of 1% low melting point on agarose gel, purified on an Elutip (Schleicher and Schuell, Keene, N.H.). After ethanol precipitation, the Cla I fragment was resuspended in ligation buffer (T. Maniatis et al, op cit) and mixed with the cut vector. The solution was incubated with T-4 ligase (Bethesda Research Laboratories, Gaithersburg, Md.) and the resulting recombinant DNA used to transform Escherichia coli strain RR1 cells, A.T.C.C. No. 31447 by standard procedures (T. Maniatis et al., op cit). Two hundred five colonies which were resistant to 25 μg/ml ampicillin were obtained. Plasmid DNA was isolated from 12 colonies by the boiling procedures of Holmes and Quigley [Anal. Biochem. (1981) 114:193] and analyzed by restriction endonuclease mapping. One plasmid (pMC2) has the Cla I insert as indicated in FIG. 3.

EXAMPLE 4

Recombinant Plasmid pSM7

Figure 4:
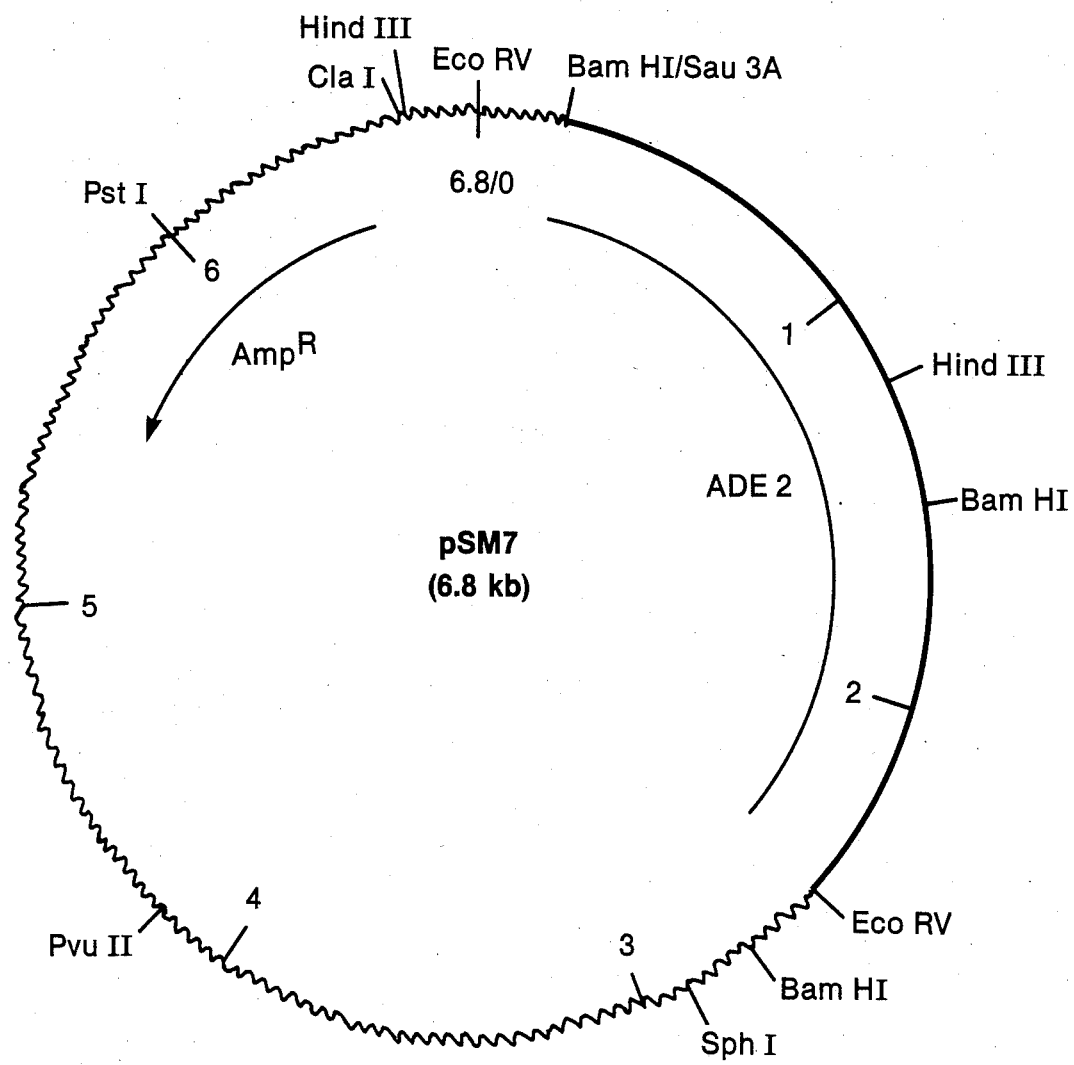
FIG. 4 illustrates the structure of recombinant plasmid pSM7.

The construction of pSM7 was accomplished by combining the 2.5 kb. EcoRV fragment of pMC2 derived from Candida DNA and a small portion of pBR322 DNA with the cloning vehicle pBR322. Two μg of pMC2 was cut with restriction enzyme EcoRV using medium salt buffer conditions (T. Maniatis et al., op cit), phenol extracted, ethanol precipitated and resuspended in 10 μl ligation buffer. The solution was incubated with T-4 ligase (Bethesda Research Laboratories, Gaithersburg, Md.) and the resulting recombinant DNA used to transform Escherichia coli strain RR1 cells, A.T.C.C. No. 31447 by standard procedure (T. Maniatis et al., op cit). Over 3000 colonies resistant to 25 μg/ml ampicillin were obtained. Plasmid DNA was isolated from 15 colonies and analyzed by restriction endonuclease mapping. One plasmid (pSM7) has the EcoRV insert indicated in FIG. 4.

EXAMPLE 5

Transformation of Candida albicans hOG300 with pMK3

Candida albicans strain hOG300 (ade 2, pro, met, bio) was grown overnight in YEPD (1% Bacto-yeast extract, 2% Bacto-peptone, 2% dextrose) with 20 mg/ml adenine sulfate at 30° C. to late log stage. Four flasks of 50 ml YEPD and adenine were inoculated with 0.75 ml each of the overnight culture and incubated at 30° C. for five hours to reach a cell density of $1 \times 10^7$/ml. Cells were harvested by spinning at 8000 rpm for five minutes. The yeast was resuspended in 10 ml of SED (1 M sorbitol, 25 mM EDTA pH 8.0, 50 mM dithiothrietol) and incubated for ten minutes at 30° C. The cells were pelleted and resuspended in 10 ml SCE (1 M sorbitol, 0.1 M sodium citrate buffer pH 5.8, 10 mM EDTA) with 100 μl of filter-sterilized crude solution of β-glucuronidase from Helix pomatia (Sigma, St. Louis, Mo.). After incubation at 30° C. for 30 minutes, the protoplasts were gently pelleted by centrifugation, resuspended in 10 ml CaS (1 M sorbitol, 10 mM CaCl$_2$ and 10 mM Tris HCl, pH 7.5) and pelleted again. The protoplasts are resuspended in 1.0 ml CaS and 10 μl dimethylsulfoxide added, after which the mixture is placed in a 37° C. water bath for 30 seconds. The suspension was divided into two parts, one receiving 70 μl of pMK3 (1.0 mg/ml) in TE (10 mM Tris HCl, pH 8.0, 1 mM EDTA) the other receiving 70 μl TE. Both samples are incubated on ice for 30 minutes, heat shocked for 30 seconds at 42° C. and then mixed with 5 ml of 20% (w/v) polyethylene glycol 4000 solution. After thorough mixing, the protoplasts were incubated for 20 minutes at room temperature, pelleted gently and resuspended in 0.6 ml of recovery medium (1 M sorbitol 33%, v/v YEPD, 6.7 mM CaCl$_2$ and 20 mg/ml adenine sulfate). The cells were incubated for 30 minutes at 30° C. and then were plated either directly on the surface of minimal medium SD (0.67% Bacto-yeast nitrogen base without amino acids, 2% dextrose, 2% bacto-agar) supplemented with 1 M sorbitol, proline, 400 mg/L, methionine, 20 mg/L, biotin, 2 μg/ml and casamino acids 200 mg/L) or mixed with 48° C. molten supplemented SD agar and poured into petri plates. Both plating methods yield 3-6 adenine prototrophs per 10$^6$ regenerable protoplasts, approximately 0.5-5 transformants/μg plasmid DNA. The aliquot which received no DNA gave no colonies. The presence of YEp13 sequences in the adenine prototrophs was scored by hybridization with a radiolabelled probe in a colony hybridization analysis. Colony hybridization of C. albicans was performed by streaking cells on YEPD (1% yeast extract, 2% peptone, 2% glucose) solidified with 2% agarose and growing for 2 days at 30° C. Colonies were transferred to Gene Screen nylon membranes (New England Nuclear, Boston, Mass.) by overlaying with membranes and continuing incubation for one day. The transferred cells were lysed in situ by first pretreating it with 50 mM EDTA and and 15% β-mercaptoethanol for 15 minutes at room temperature and then digesting cell walls with 1 mg/ml zymolyase 5000 (Miles, Naperville, Ill.) in 1 m sorbitol, 20 mM EDTA. Incubation for 3 hours at 37° C. resulted in protoplast formation as determined by microscopic observation. The DNA containing membranes were treated according to the procedures recommended by the manufacturer. Hybridization with pMK3 labelled by nick translation were performed by standard procedures (T. Maniatis et al., op cit). Thirteen of 26 prototrophs obtained by transformation with pMK3 gave a positive signal with the YEp13 probe, while all 26 were positive with a pMK3 probe (Table I).

Total DNA prepared from three of the pMK3 transformants with YEp13 sequences were further analyzed by gel blots. Total genomic DNA from C. albicans was prepared by the method described in Example 1. Undigested, Cla I, - Pvu II, Hind III, Bam HI and Eco RV - digested DNA's were hybridized with radiolabelled YEp13, pMK3 or pMCI DNA.

Hybridization with YEp13 with undigested DNA occurred at the position of chromosomal DNA indicating that these sequences had been integrated into the genomic DNA. No hybridization with lower molecular weight bands could be observed even with extended exposure of the autoradiograms. Restriction analysis indicated that the transformants arose by a single recombination event at the homologous region, retaining the entire YEp13 sequence. For example, Cla I digestion of pMK3 yields four fragments of 5.2, 6.0, 2.5 and 2.0 kb. These four bands plus the two flanking fragments at the site of integration should be revealed when Cla I cut DNA from the transformants is hybridized with labelled pMK3. When probed with pMK3, transformant DNA showed the expected two additional bands which have the same mobility as the host ADE 2 region band. No other bands are seen. These results are consistent with one or several tandem copies integrated at the site of the resident ADE 2 gene.

Similar conclusions can be drawn from the Bam HI, Eco RV and Hind III digestion results. Twenty-six pMK3 transformants were tested for stability by growing for 20 generations in rich medium and plating onto selective and non-selective media. No ade 2− segregates were detected for 24 of the strains (>100 isolates tested). Two of the strains gave rise to ade 2− segregants at a rate of 1% and 5%. These results are also consistent with an integrative transformation event.

EXAMPLE 6

Transformation with Linear Plasmids

Linear plasmid was prepared from pMC2 by cutting in the unique Kpn I site within the *Candida albicans* portion of the DNA, but outside the complementing region. Twenty-five μg of pMC2 was digested with 80 units of Kpn I in low salt buffer for two hours at 37° C. (T. Maniatis, op cit). The enzyme was inactivated by phenol extraction with the DNA and ethanol precipitated for further purification. The dried precipitate was resuspended in 50 μl 10 mM Tris HCl pH 8.0 1 mM EDTA. One-half was used to transform *Candida albicans* strain A81-pu (ade 2) and the other half to transform *Candida albicans* strain hOG300 (ade 2, met, pro, bio) by the following modifications of the procedure in Example 5. One flask of 50 ml YEPD) medium (1% Bacto-yeast extract, 2% Bacto-peptone, 2% dextrose) with 20 mg/ml adenine sulfate was inoculated with 1 ml fresh overnight culture of *Candida albicans*. After growth at 30° C. for five hours, the cell density was approximately $1.5 \times 10^7$ cells/ml. The cells were harvested and protoplasts prepared from them as described in Example 5. The protoplasts are washed once with 5.0 ml CaS (1 M sorbitol, 10 mM CaCl$_2$ and 10 mM Tris HCl, pH 7.5) and resuspended in 0.5 ml CaS. Three aliquots of 0.1 ml of protoplast suspension were used for incubation with 10 μg pMC2 DNA (uncut), 12.5 μg pMC2 DNA (Kpn I cut) and no DNA as control for 15 minutes at room temperature. Then 1.0 ml polyethylene glycol 4000 (20% solution w/v) was added. After thorough mixing, the protoplasts with fused DNA were incubated for 20 minutes at room temperature, pelleted gently and resuspended in 0.6 ml recovery medium (1 M sorbitol, 33% v/v YEPD, 6.7 mM CaCl$_2$ and 20 mg/ml adenine sulfate. The remainder of the procedure was the same as detailed in Example 5. The data in Table II shows that linear plasmids have enhanced transformation frequencies. Colony hybridization analysis (as described in Example 5) confirmed that the increased number of ADE 2+ colonies is due to incorporation of plasmid DNA. Approximately 50% of the *Candida albicans* strain hOG300 transformants have plasmid sequences whether cut or uncut vector is used as transforming DNA.

TABLE II

| Transformation of *Candida albicans* with Linear Plasmids | | |
|---|---|---|
| Strain | Plasmid DNA | ADE+ Transformants |
| hOG300 | pMC2 uncut | 16 |
| | pMC2 KpnI cut | 72 |
| | 0 | 10 |
| A81-pu | pMC2 uncut | 19 |
| | pMC2 KpnI cut | 46 |
| | 0 | 10 |

EXAMPLE 7

Enhanced Transformation Frequencies with Carrier DNA

Carrier DNA was prepared from purchased *Escherichia coli* strain B DNA (Sigma, St. Louis, Mo.). A 1 mg/ml solution in TE (10 ml Tris HCl, pH 8.0, 1 mM EDTA) was sonicated for 5 minutes with a 50% pulse cycle. The solution was maintained in a salt-ice bath to prevent overheating. The DNA was ethanol precipitated, washed with 70% ethanol, dried and resuspended in TE. The final concentration was determined spectrophotometrically as 0.8 mg/ml.

Protoplasts of *Candida albicans* DKY-129 (ade 2, pro bio) A.T.C.C. No. 20,735 were prepared according to the method described in Example 6. One aliquot of protoplasts was transformed by the method of Example 6 with 5 mg plasmid pMC2. Another aliquot was transformed with 5 mg plasmid pMC2 with 20 μg *E. coli* DNA. A control aliquot was transformed with *E. coli* DNA but no plasmid DNA. Another control aliquot received no exogeneous DNA. The data in Table III show that exogenous carrier DNA enhances transformation frequency.

TABLE III

| Enhanced Transformation with Carrier DNA | | |
|---|---|---|
| Plasmid DNA | Carrier DNA | Transformants |
| pMC2 | 0 | 5 |
| pMC2 | + | 43 |
| 0 | + | 1 |
| 0 | 0 | 1 |

EXAMPLE 8

Cloning *Candida albicans* DNA Sequences which Enhance Transformation

*Candida albicans* DNA from strain SC5314 was prepared according to the procedure in Example 1. Strain SC5314 was originally isolated from a patient with disseminated candidiasis, has no known mutations, and has been maintained in the Culture Collection of E. R. Squibb & Sons, Inc. Princeton, N.J. Three μg pMC2 DNA was cut in 15 μl of medium salt buffer with restriction endonuclease Pvu II which produces blunt ends (T. Maniatis et al., op cit). Twelve μg of *Candida albicans* SC5314 total genomic DNA was digested to completion with Rsa I which recognizes a four base pair sequence and also produces blunt ends. The fragments produced were less than 1.5 kb in length. The enzymes were inactivated by phenol extraction and the DNA concentrated by ethanol precipitation. The dried DNA fragments were resuspended in 30 μl ligation buffer with three units of T-4 ligase (Bethesda Research Laboratories, Gaithersburg, Md.) and incubated overnight at 9° C. The recombinant DNA mix was used to transform *E. coli* RRI, A.T.C.C. No. 31447 cells and ampicillin resistant transformants were selected. Four thousand individual transformants were recovered. Plasmid from 15 colonies chosen at random was isolated by the rapid boiling procedure of Holmes and Quigley [Anal. Biochem. (1981)114:193]. The restriction enzyme nuclease pattern of the plasmids indicated that at least 30% had inserts. The 4000 *E. coli* transformants were pooled and a large scale plasmid preparation made from them (T. Maniatis et al., op cit). 12.5 µg of plasmid DNA were used to transform *Candida albicans* strain hOG300 (ade 2, pro, met, bio) by the procedure described in Example 6 to adenine prototrophy. The hOG300 prototrophs were pooled and total DNA prepared from them. Total Candida DNA was isolated according to the procedure detailed in Example 1.

If the original library had plasmids capable of autonomous replication or plasmids which were unstably integrated into the *Candida albicans* hOG300 chromosome, they would be present as free plasmids in the total DNA preparation. Free plasmids can be detected in the total DNA preparation by their ability to transform *E. coli* cells. When 1 µl of total DNA was used to transform *E. coli* RR1, A.T.C.C. No. 31447, cells to ampicillin resistance 34 colonies were recovered. The plasmids from each of these colonies were isolated and analyzed by restriction mapping. Those plasmids having similar restriction patterns were pooled and tested for the ability to transform *Candida albicans* at a greater frequency than pMC2. One pool had a slightly higher frequency and the individual plasmids of this were tested. One of these plasmids, pSM8, transformed *Candida albicans* strain hOG300 at a frequency of 47 ADE 2+ transformants/µg plasmid DNA compared to 2 ADE 2+ transformants/µg plasmid with pMC2. When 20 µg of sonicated *E. coli* DNA was added with pSM8, DNA frequencies of 200 transformants/µg plasmid DNA were obtained. Other fragments of Candida DNA can also increase transformation frequency. However, the pSM8 transformants were stable even after 20 generations of non-selective growth. This suggests that although plasmid DNA was recoverable from *Candida albicans* after transformation, this must later lead to an integration event as the ADE 2+ phenotype is stable.

What is claimed is:

1. A plasmid comprising a fragment of DNA from *Candida albicans* containing the intact ADE 2 gene.

2. *Candida albicans*, having inserted therein a plasmid comprising a fragment of DNA from *Candida albicans* containing the intact ADE 2 gene.

3. A method of introducing exogenous DNA into *Candida albicans* comprising:
   (i) enzymatically removing the cell wall of *Candida albicans*;
   (ii) adding exogenous DNA to the resultant *Candida albicans* spheroplasts;
   (iii) fusing the exogenous DNA with the *Candida albicans*; and
   (iv) selecting the *Candida albicans* cells having the exogenous DNA incorporated therein.

4. A method in accordance with claim 3 wherein the exogenous DNA is added as a plasmid comprising a fragment of DNA from *Candida albicans* containing the intact ADE 2 gene.

5. A method in accordance with claim 3 wherein the exogenous DNA is contained in a plasmid which has been linearized.

6. A method in accordance with claim 3 which further comprises the addition of non-transforming DNA.

7. A method in accordance with claim 3 wherein the exogenous DNA is added as a plasmid comprising a fragment of DNA from *Candida albicans* containing sequences which enhance transformation frequencies.

* * * * *